(12) United States Patent
Trahern

(10) Patent No.: US 10,182,624 B2
(45) Date of Patent: Jan. 22, 2019

(54) MULTIPLY FUNCTIONING FINGER RING

(71) Applicant: Robert T. Trahern, Sublette, KS (US)

(72) Inventor: Robert T. Trahern, Sublette, KS (US)

( * ) Notice: Subject to any disclaimer, the term of this patent is extended or adjusted under 35 U.S.C. 154(b) by 0 days.

(21) Appl. No.: 15/845,818

(22) Filed: Dec. 18, 2017

(65) Prior Publication Data

US 2018/0103733 A1    Apr. 19, 2018

(51) Int. Cl.
*A44C 9/02*    (2006.01)
*A44C 9/00*    (2006.01)
*A41D 13/08*    (2006.01)

(52) U.S. Cl.
CPC .......... *A44C 9/0015* (2013.01); *A41D 13/087* (2013.01); *A44C 9/02* (2013.01)

(58) Field of Classification Search
CPC ..... A44C 9/0015; A44C 9/003; A44C 9/0053; A44C 9/0084; A44C 9/02; A41D 13/087; B43K 23/012; B42D 9/04
USPC .................................................. 294/25; 2/21
See application file for complete search history.

(56) References Cited

U.S. PATENT DOCUMENTS

| | | | |
|---|---|---|---|
| 421,665 A * | 2/1890 | Buchman | |
| 805,664 A | 11/1905 | Ramage | |
| 922,954 A | 5/1909 | Rives | |
| 931,511 A * | 8/1909 | Southworth | |
| 1,174,887 A * | 3/1916 | Meriwether | A61F 13/105 131/186 |
| 1,268,103 A * | 6/1918 | Fleming | A41D 13/087 2/21 |
| 2,735,321 A | 2/1956 | Browne | |
| 3,596,964 A | 8/1971 | Zazzara | |
| 4,507,804 A * | 4/1985 | Consigny | A41D 13/087 2/163 |
| 5,070,563 A | 12/1991 | Tervola | |
| 5,186,189 A * | 2/1993 | Harris | A45D 29/00 132/285 |
| 5,220,690 A * | 6/1993 | Hoos | A41D 13/087 2/160 |
| 5,885,018 A | 3/1999 | Sato | |
| 7,614,252 B2 | 11/2009 | DeLyrot | |
| D653,580 S | 2/2012 | Hustik | |
| 8,262,599 B2 | 9/2012 | Chandrasekar et al. | |
| D676,777 S | 2/2013 | Williams | |

(Continued)

FOREIGN PATENT DOCUMENTS

DE    102014003820    9/2015
GB    190900804    5/1909

(Continued)

*Primary Examiner* — Dean J Kramer
(74) *Attorney, Agent, or Firm* — Kenneth H. Jack; Davis & Jack, L.L.C.

(57) ABSTRACT

An assembly for ornamenting a proximal end of a finger and for enhancing friction at the distal end of the finger, the assembly incorporating first and second bands; a void within the second band for receiving and releasing the finger; a frictional crown attached to the second band; and a shaft having an anchor end pivotally attached to the first band and having an opposite end pivotally attached to the second band, the shaft being adapted for guiding, orbiting, and counter-orbiting movements of the second band between flexed and extended positions, wherein in the flexed position, the crown overlies the proximal end of the finger, and wherein in extended position, the crown overlies the finger's distal end.

11 Claims, 3 Drawing Sheets

(56) References Cited

U.S. PATENT DOCUMENTS

| | | |
|---|---|---|
| 8,584,298 B2 | 11/2013 | Viscomi et al. |
| 8,887,970 B2 | 11/2014 | Tsai et al. |
| 9,496,909 B2 | 11/2016 | West |
| 9,723,910 B2 | 8/2017 | Due |
| 2009/0270050 A1 | 10/2009 | Brown |
| 2013/0146625 A1 | 6/2013 | Karle et al. |
| 2015/0000686 A1 | 1/2015 | Bajaj et al. |
| 2015/0342328 A1 | 12/2015 | Seger |
| 2016/0045019 A1 | 2/2016 | Srey |

FOREIGN PATENT DOCUMENTS

| | | |
|---|---|---|
| JP | 2010207332 | 9/2010 |
| WO | WO9910133 | 4/1999 |
| WO | WO2015055870 | 4/2015 |
| WO | WO2017081071 | 5/2017 |

* cited by examiner

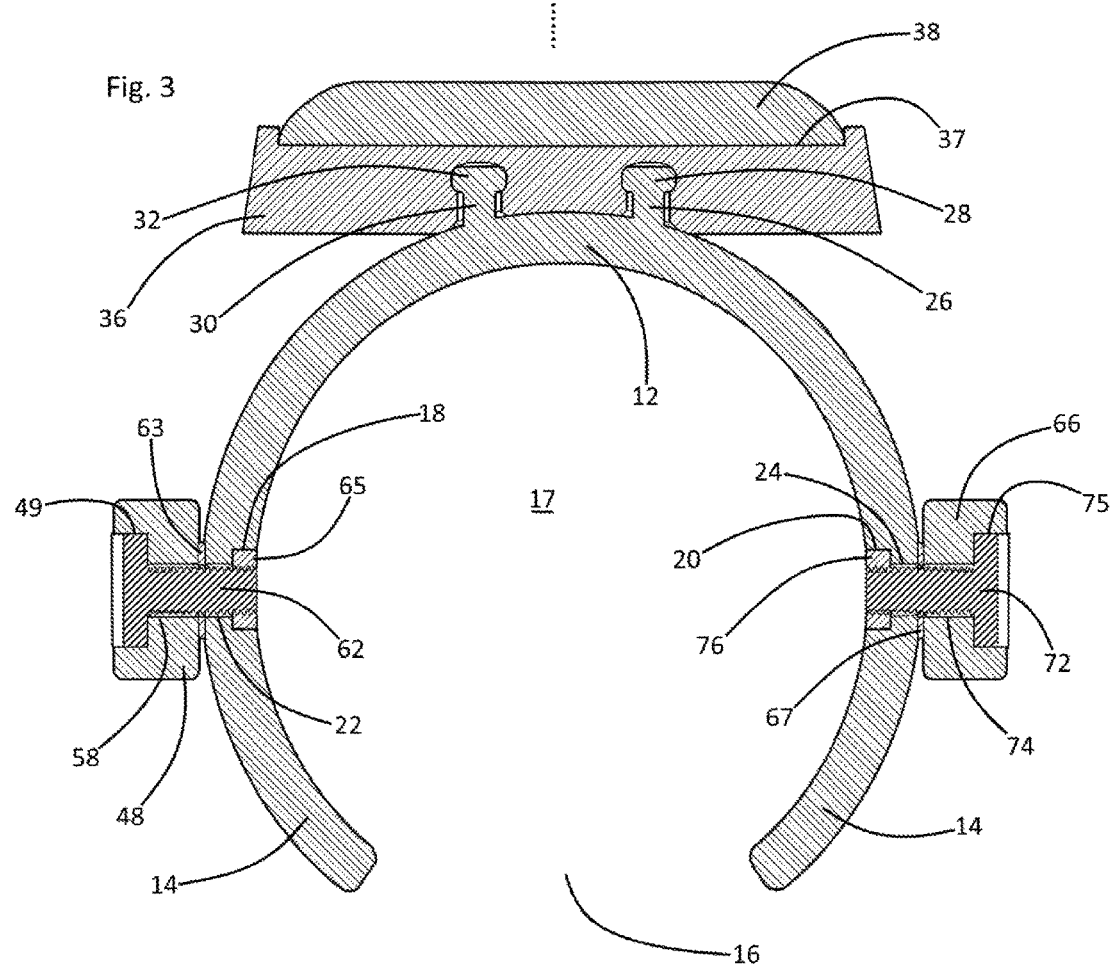

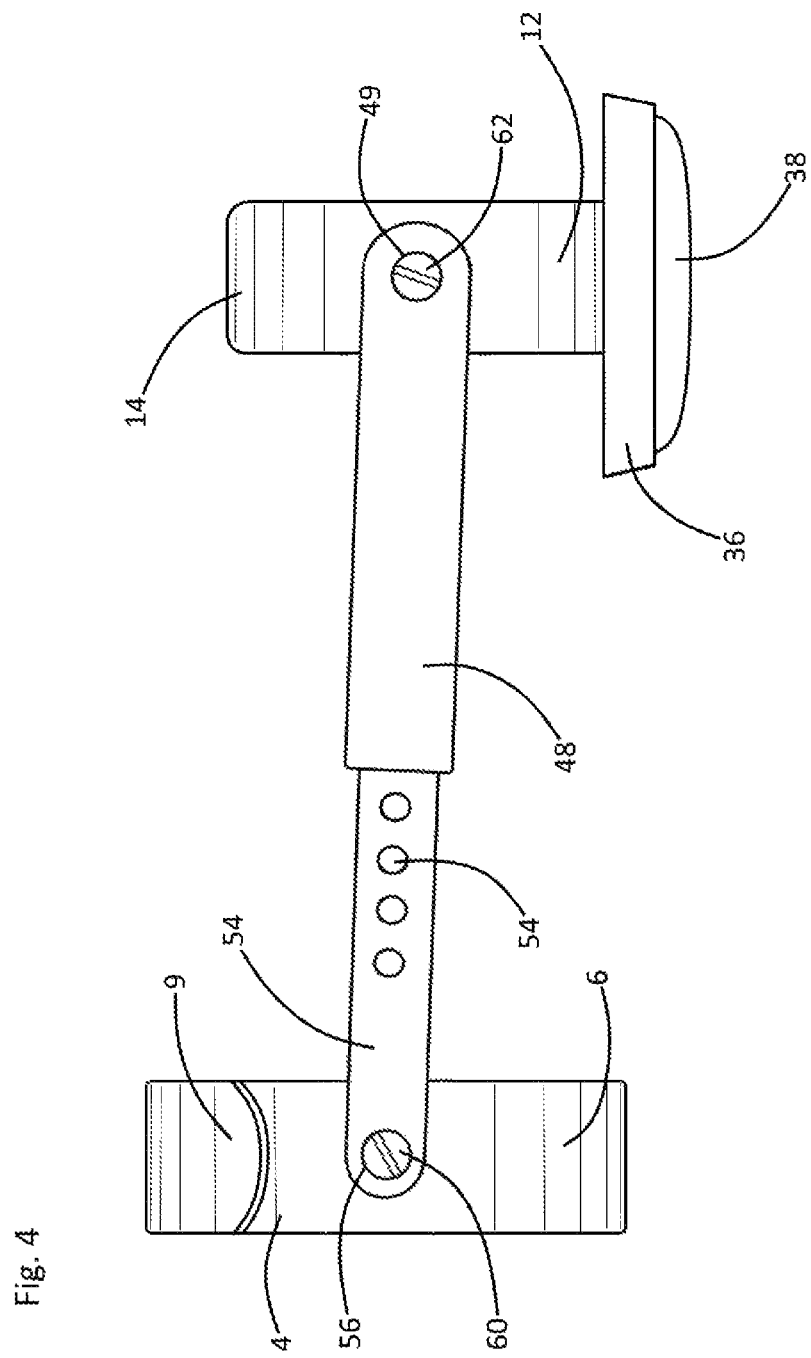

MULTIPLY FUNCTIONING FINGER RING

FIELD OF THE INVENTION

This invention relates to finger rings. More particularly, this invention relates to such rings which are adapted for additionally functioning for enhancing the finger's ability to grasp and manipulate objects.

BACKGROUND OF THE INVENTION

Conventional finger rings are known to perform a function of ornamenting a dorsal aspect or back-of-hand side of a wearer's finger or phalange. Such conventional finger rings typically are mechanically incapable of performing any other or additional function in relation to the function of the finger on which the ring is worn. The instant inventive multiply functioning finger ring incorporates additional and unique structures into a finger ring causing the ring to constitute a mechanical assembly which may additionally and alternatively function as a fingertip friction enhancing device.

BRIEF SUMMARY OF THE INVENTION

The instant inventive multiply functioning finger ring preferably comprises an assembly of structural components which is specially adapted for alternatively performing a conventional ornamenting function at a dorsal aspect of a proximal end of a ring wearer's finger or phalange, and for enhancing fingertip friction at the palmar aspect of the finger's distal end. In a preferred embodiment, the inventive assembly comprises first and second bands which respectively have upper and lower shanks or upper and lower ends.

Further structural components of the instant inventive assembly comprise first means for alternatively receiving and releasing the finger upon which the assembly is worn. Such receiving and releasing means are preferably connected operatively to or are formed wholly with or integrally as a part of the assembly's second band component. In a preferred embodiment, such first means comprise a void or open space positioned at the lower end of the second band, such void allowing lateral and oppositely lateral arcs of such band to splay away from each other for finger insertions.

A further structural component of the instant inventive assembly comprises a crown which is preferably decorative and has a friction enhancing upper surface. In a preferred embodiment, such friction enhancing upper surface comprises a pad or layer of a high friction elastomeric material such as synthetic rubber. The crown is preferably fixedly attached to the upper end of the second band.

A further structural component of the instant inventive assembly comprises at least a lateral shaft, and preferably both such lateral shaft and an oppositely lateral shaft. In the preferred embodiment, radially inner ends or anchor ends of such shafts are pivotally attached to laterally opposed sides of the first band. The opposite ends of such shafts (i.e., the shafts' orbiting ends) are necessarily attached to the second band, and those attachments are preferably pivoting joints which are positioned at laterally opposed sides of the second band. In the preferred embodiment, such shafts are adapted for, upon an annular positioning of the first band about the middle portion of the wearer's finger, guiding orbiting and counter-orbiting movements of the second band between a flexed position and an extended position.

Upon pivoting and orbital movements of the shafts and the attached second band toward their flexed positions, the open void of the second band may receive the proximal end of the finger, allowing the second band to securely grasp the finger. Such orbiting positioning of the second band allows the decorative crown component to overlie the dorsal aspect of the finger. Accordingly, upon a pivoting execution of such orbiting and flexing motion, the instant inventive assembly may advantageously perform a function of finger ring ornamenting.

Upon opposite or counter-orbiting pivoting of the shafts and second band to their extended positions, the second band distally pivots with respect to the distal extension of the finger. During such pivoting, the second band may swivel upon its preferably provided pivot mounts to allow the second band to receive the finger at its tip or distal end. Such pivoting advantageously causes the high friction crown to invert and to underlie the fingertip. Such counter-orbiting pivotal positioning of the assembly allows the preferred high friction character of the crown to provide a relatively high friction surface (relative to skin friction) for fingertip contacts. Accordingly, the instant inventive assembly allows a relatively low friction object such as a cell phone to be securely held and manipulated in a slip free fashion.

Accordingly, objects of the instant invention include the provision of a multiply functioning finger ring which incorporates structures as described above, and which arranges those structures in relation to each other in the manners described above for the performance of the beneficial functions described above.

Other and further objects, benefits, and advantages of the instant invention will become known to those skilled in the art upon review of the Detailed Description which follows, and upon review of the appended drawings.

BRIEF DESCRIPTION OF THE DRAWINGS

FIG. 2 is a sectional view of a crown component in accordance with FIG. 1.

FIG. 3 is an alternative sectional view in accordance with FIG. 1.

FIG. 4 is a side plan view of the structure of FIG. 1, the view showing a reconfiguration of components.

DETAILED DESCRIPTION OF A PREFERRED EMBODIMENT

Figure 1:
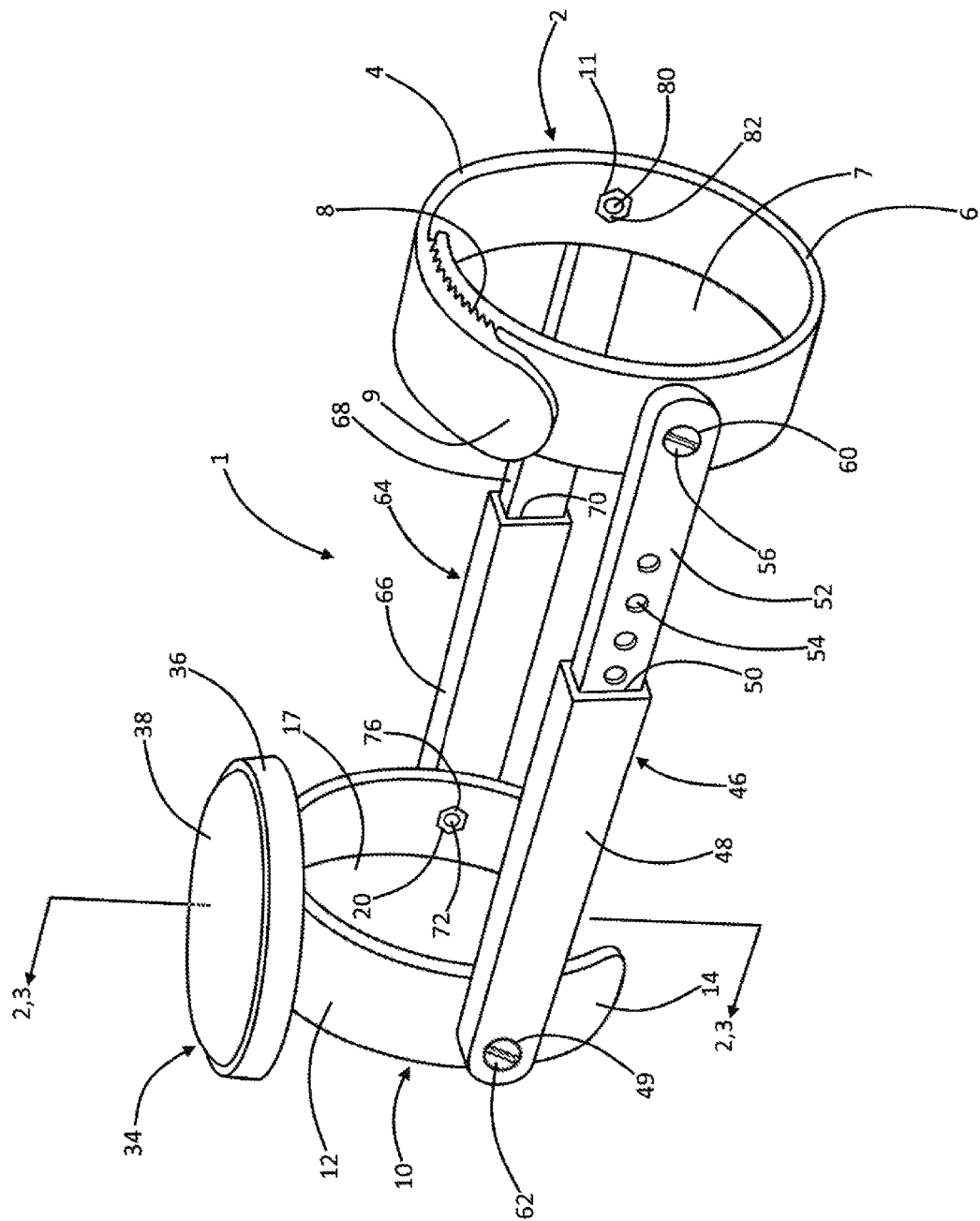
FIG. 1 is a perspective view of a preferred embodiment of the instant inventive multiply functioning finger ring.

Referring now to the drawings and in particular to Drawing FIG. 1, a preferred embodiment of the instant inventive multiply functioning finger ring is referred to generally by Reference Arrow 1. Referring further simultaneously to FIG. 4, a first structural component of the assembly 1 comprises a first band which is referred to generally by Reference Arrow 2, such band having an upper portion or upper shank 4 and having a lower portion or lower shank 6. Suitably, the first band 2 may comprise a continuous annular loop or ring. However, as depicted, the first band preferably incorporates series of interlocking teeth 8 which may clamp the lateral and oppositely lateral extensions of the upper shank 4 at a multiplicity of manually selectable finger circumference fitting sizes. Upward pulling upon tab 9 effectively releases the teeth 8 for adjustment and readjustment of the effective circumference of band 2. In a preferred embodiment, the first band 2 has an oppositely lateral inner surface recess 11 which receives and securely holds helically threaded hex nut 82, and similarly has a lateral nut receiving recess (not within views). Such recesses 11 and nuts 82 comprise swivel joint components whose functions are further explained below.

Referring simultaneously to all figures, a further structural component of the instant inventive assembly comprises a second band which is referred to generally by Reference Arrow 10, such band 10 having an upper shank portion 12, and a lower shank portion 14. In a preferred embodiment, the lower shank portion 14 of the second band 10 includes a lower opening or void 16 which allows lateral and oppositely lateral sides of the band 10 to be splayed for widening of opening 16 to facilitate an upward receipt of a phalange or finger into space 17. The opening or void 16 constitutes a first finger receiving and releasing means component of the instant inventive assembly, such means component being formed integrally with band 10. Alternatively, such means component may suitably be configured similarly with the first band's interlocking teeth adjustable fastener 8, such fastener type being representative of the invention's second means for finger receipt and release.

Lateral and oppositely lateral sides of the second band 10 preferably include swivel screw receiving apertures 22 and 24, such apertures enlarging at their inner ends to form fitted hex nut receiving recesses 18 and 20. Lateral and oppositely lateral snap fastener posts 30 and 26 having enlarged heads 32 and 28 (the functions of which are explained below) preferably extend upwardly from the upper end or upper shank 12 of band 10.

A crown component of the instant inventive assembly is referred to generally by Reference Arrow 34. In a preferred embodiment, the crown 34 comprises a disk shaped (or other geometric configuration) base 36 having an upwardly opening pad receiving recess 37. A high friction elastomeric pad or layer 38 is nestingly received within recess 37, and such pad is preferably adhesively bonded in place. The upper end or shank 12 of band 10 preferably is upwardly receivable within recess 40, and lateral and oppositely lateral snap sockets 44 and 42 which open within recess 40 may simultaneously receive snap posts 30, 32, 26, and 28. Movement of the crown 34 which is manually driven downwardly from the overlying FIG. 2 position toward the FIG. 3 position may effectively and securely releasably snap the crown 34 in place upon band 10 as indicated in FIG. 3. The snap fastener components 26,28,30,32,40,42,44, are considered as being representative of other suitably substituted connectors and fasteners which are capable of securely and releasably interconnecting the crown 34 upon the band 10. Suitably, the crown 34 may be alternatively rigidly wholly formed with the second band 10, or may be permanently adhesively bonded to band 10. Such rigid alternative attachments and the releasable snap fasteners depicted in FIGS. 2 and 3 are considered to be alternative representations of the instant invention's attaching means component.

A lateral shaft component of the instant inventive assembly is referred to generally by Reference Arrow 46, such shaft 46 preferably comprising a telescoping or alternatively extending and retracting element. In a preferred embodiment, the lateral shaft 46 is configured as a quill 48 and stem 52 combination wherein the quill 48 has a hollow bore 50, and wherein the stem 52 is closely fitted for nesting and sliding receipt within quill 48. In a preferred embodiment, the quill component 48 includes an interior lug or detent element (not depicted within views) which extends inwardly from an inner wall of quill 48. Such lug or detent may selectively engage recess series 54 for adjusting the overall length of the lateral shaft 46.

A swivel screw 60 preferably extends oppositely laterally through the pivoting anchor end of shaft 46, the head of such screw 60 preferably unobtrusively nesting within recess 56. At the opposite or orbiting end of shaft 46, a swivel screw 62 similarly extends oppositely laterally, the head of such screw 62 being similarly unobtrusively nested within recess 49. From such recess 49, the swivel screw 62 further extends oppositely laterally through an aperture 58 within the orbiting end of quill 48.

In the preferred embodiment, an oppositely lateral shaft, referred to generally by Reference Arrow 64, is additionally provided for the purpose of enhancing the lateral stability of the assembly 1. The oppositely lateral shaft 64 preferably includes a quill 66 having a hollow bore 70, such bore being closely fitted for slidably receiving a telescoping stem 68. A swivel screw 80 extends laterally through the anchor end of shaft 64, and such screw 80 is preferably threadedly received within the hex nut 82 which is unobtrusively nestingly received within and held against rotation by the recess 11. Swivel screw 72 at the opposite orbiting end of shaft 64 similarly oppositely laterally extends through recess 75 and through aperture 74, the inner end of such screw 72 being threadedly received by a nut 76 which is received within recess 20.

Lateral and oppositely lateral washers 63 and 67 preferably provide rotary bearing surfaces for swiveling motions of the second band 10 with respect to the orbiting ends of shafts 46 and 64. Similar washers (not depicted within views) are preferably provided for facilitating rotary motions of the first band 2 with respect to the anchor ends of shafts 46 and 64.

In use of the instant inventive assembly 1, a wearer may initially grasp band 2 and may utilize a fingernail for upwardly pulling upon tab 9 in order to disengage teeth 8. Thereafter, the wearer may extend one of his or her fingers (the middle finger of the left hand for example) forwardly or distally into the central space 7 of the first band 2.

Thereafter, the wearer may squeeze the lateral and oppositely lateral sides of the first band 2 toward each other causing teeth 8 to engage each other and to progressively reduce the effective circumference of the first band 2. The progressive engagement of teeth 8 preferably continues until the interior circumference of the band 2 closely matches the circumference of the wearer's middle finger.

In the preferred embodiment, such middle finger mounting of the first band 2 positions such band 2 so that it annularly extends about the finger's middle phalangeal portion between the finger's proximal and distal inter-phalangeal joints. Upon such mounting and positioning, slight diameter enlargements which are commonly present at the finger's proximal and distal inter-phalangeal joints may advantageously serve as slide stops for preventing the first band 2 from excessively sliding distally or proximally along the finger during use of the inventive assembly.

Thereafter, the user may simultaneously pivot or orbitally move the lateral and oppositely lateral shaft components 46 and 64 in the counter-clockwise direction (or in the proximal direction) about the shaft anchoring swivel screws 60 and 80, such orbiting motions constituting a flexing motion with respect to the finger. Upon such motion, the second band 10 orbits toward the proximal end of the user's finger, and upon completion of such motion, the dorsal aspect of the user's finger enters and passes through the void or opening 16, allowing the finger to securely reside within ring space 17.

In a preferred mode of utilization of the instant inventive assembly 1, the wearer may, immediately prior to inducing the above described orbiting motions of shafts 46 and 48, telescopingly adjust the effective lengths of such shafts. In a preferred usage mode, such telescoping manipulating of shafts adjusts their lengths so that they hold the second band 10 at a location at which they may encircle the finger's proximal phalanx portion between the fingers' metacarpophalangeal and proximal interphalangeal joints. Slight finger diameter enlargements which are commonly present at such metacarpophalangeal and proximal interphalangeal joints may advantageously resist proximal and distal sliding motions of the second band 10 along the finger. Upon completion of such orbital positioning of shafts 46 and 64, and of band 10, the crown 34 overlies the dorsal aspect of the proximal end of the finger. Such positioning advantageously allows the crown 34 to perform a conventional finger ornamenting function.

In the event that the wearer wishes to grasp a smooth or slippery object such as a cell phone, the wearer may grasp the second band 10 and may pull upwardly thereon, causing the finger to exit space 17 through opening 16, and disengaging the band from the proximal end of the wearer's finger. Upon such disengagement, the band 10, the crown 36, and the shafts 46 and 64 freely counter-orbit about lateral and oppositely lateral swivel screws 60 and 80. Such counter-orbiting motions constitute extension motions with respect to the finger. The counter-orbiting extension of the assembly preferably continues until the band 10 and crown 34 reside at the distal phalanges portion of the finger. Similarly with the above described telescoping adjustments of shafts 46 and 64 for proximal phalangeal positioning of the second band 10, such shafts may be preliminarily telescopingly adjusted so that crown 34 and its frictional pad 38 overlie in the palmar direction the user's fingertip.

Referring in particular to FIG. 3, upon such telescoping readjustment and upon such counter-orbiting positioning of the second band 10, downwardly directed fingertip pressure applied to the inner periphery of such band may effectively press the high friction elastomeric pad 38 against a relatively slippery surface such as the cell phone's screen. During such frictional contact, annular holding forces applied by bands 2 and 10 to the finger, combined with the functions of shafts 46 and 64 as ties therebetween, allows the cell phone to be securely held at the wearer's fingertips.

A reversal of the assembly manipulating steps described above re-configures the assembly for conventional ring finger ornamenting use as indicated in FIG. 1.

While the principles of the invention have been made clear in the above illustrative embodiment, those skilled in the art may make modifications to the structure, arrangement, portions and components of the invention without departing from those principles. Accordingly, it is intended that the description and drawings be interpreted as illustrative and not in the limiting sense, and that the invention be given a scope commensurate with the appended claims.

The invention hereby claimed is:

1. An assembly for alternatively ornamenting at a dorsal aspect of a proximal end of a finger and enhancing friction at a palmar aspect of the finger's distal end, said assembly comprising:
   (a) first and second bands having upper and lower ends;
   (b) first means for alternatively receiving and releasing the finger, the first means for alternatively receiving and releasing the finger being formed wholly with or connected operatively to the second band;
   (c) a crown having a frictional upper surface;
   (d) attaching means interconnecting the crown and the second band, the attaching means positioning the crown over said band's upper end;
   (e) a lateral shaft having an anchor end pivotally attached to the first band, and having an opposite end attached to the second band, the lateral shaft being adapted for, upon mounting of the first band upon the finger, orbiting and counterorbiting the second band between flexed and extended positions wherein, upon the orbiting to the flexed position, the crown overlies the dorsal aspect of the proximal end of the finger, and upon the counterorbiting to the extended position, the crown overlies the palmar aspect of the finger's distal end.

2. The assembly of claim 1 wherein the attachment of the opposite end of the lateral shaft to the second band is adapted for facilitating pivoting of the second band.

3. The assembly of claim 2 further comprising an oppositely lateral shaft spanning between the first and second bands, the oppositely lateral shaft being positioned oppositely laterally from the lateral shaft.

4. The assembly of claim 3 wherein the lateral and oppositely lateral shafts are adapted for telescoping motions.

5. The assembly of claim 4 wherein the first means for alternatively receiving and releasing the finger comprise a void within the second band's lower end.

6. The assembly of claim 5 further comprising second means for alternatively receiving and releasing the finger, the second means for alternatively receiving and releasing the finger being formed wholly with or connected operatively to the first band.

7. The assembly of claim 6 wherein the second means for alternatively receiving and releasing the finger comprise an interlocking teeth fastener.

8. The assembly of claim 7 wherein the crown's frictional upper surface comprises an elastomeric pad.

9. The assembly of claim 4 wherein the adaptations of the lateral and oppositely lateral shafts for telescoping motions configure said shafts as quill and stem assemblies.

10. The assembly of claim 9 wherein the quill and stem assemblies comprise hollow bores within the quills, lugs extending into such bores, and series of detents within the stems.

11. The assembly of claim 1 wherein the attaching means comprise a snap fastener.

* * * * *